United States Patent [19]

Windawi et al.

[11] Patent Number: 4,471,141

[45] Date of Patent: Sep. 11, 1984

[54] PREPARATION OF ALDEHYDES

[75] Inventors: Hassan Windawi, Arlington Heights; Warren R. Oakdale, Des Plaines, both of Ill.

[73] Assignee: UOP Inc., Des Plaines, Ill.

[21] Appl. No.: 468,529

[22] Filed: Feb. 22, 1983

[51] Int. Cl.$^3$ ....................... C07C 45/29; C07C 45/32
[52] U.S. Cl. .................................... 568/474; 568/471
[58] Field of Search ........................ 568/471, 472, 474

[56] References Cited

U.S. PATENT DOCUMENTS

| | | | |
|---|---|---|---|
| 3,194,771 | 7/1965 | Vasser et al. | 568/474 |
| 3,198,753 | 8/1965 | Traina | 568/474 |
| 3,464,931 | 9/1969 | Aglieti et al. | 568/474 |
| 3,716,497 | 2/1973 | Courty | 568/474 |
| 4,355,187 | 10/1982 | Baltes et al. | 568/474 |

FOREIGN PATENT DOCUMENTS

| | | | |
|---|---|---|---|
| 1162343 | 2/1964 | Fed. Rep. of Germany | 568/474 |
| 1693092 | 1/1973 | Fed. Rep. of Germany | 568/474 |
| 2630928 | 1/1978 | Fed. Rep. of Germany | 568/474 |
| 1537140 | 7/1968 | France | 568/474 |

Primary Examiner—Werren B. Lone
Attorney, Agent, or Firm—James R. Hoatson, Jr.; Raymond H. Nelson; William H. Page, II

[57] ABSTRACT

Aqueous alcoholic solutions such as hydrous alkanols may be converted to the corresponding aldehyde in a process which involves high conversion levels and high selectivity levels by treating the solution with an oxygen-containing gas in the presence of a catalyst comprising at least two oxides of metals selected from the group consisting of molybdenum, tungsten, cobalt, nickel, manganese, iron and chromium, one of said oxides being molybdenum oxide or tungsten oxide composited on a high surface area support. Reaction conditions which are employed in the process will include temperatures in the range of from about 200° to about 400° C. and a pressure in the range of from about atmospheric to about 50 atmospheres.

5 Claims, No Drawings

PREPARATION OF ALDEHYDES

BACKGROUND OF THE INVENTION

Aldehydes comprise important chemical compounds which are useful for a variety of purposes. One source of various aldehydes comprises alcohols, the aldehydes being prepared by the oxidative dehydrogenation of the corresponding alcohols. When this type of process is employed, the oxidative dehydrogenation has been effected in the presence of catalysts such as silver catalysts, platinum black, etc. The process conditions which have been used to effect this oxidation have been in the range of from about 450° to about 550° C. The by-products which have been obtained from this reaction usually include the corresponding acids, esters, ethers, etc., the amount of said by-products being dependent to some extent upon the operating parameters employed in the reaction. In addition to the oxidative dehydrogenation of the alcohols, other methods of obtaining aldehydes have included the direct oxidation of paraffins, the hydration of alkynes utilizing mercuric sulfate or ferric sulfate catalysts, etc.

As was previously set forth, aldehydes are important articles of commerce as, for example, acetaldehyde which is used in the preparation of acetic acid, acetic anhydride, chloral, as an intermediate for drugs, perfumes, photographic agents, in phenol and urea condensation products, etc. Likewise, propionaldehyde is used in the manufacture of polyvinyl acetals and other types of plastics, in the synthesis of rubber chemicals, as a disinfectant or preservative, etc; isovaleraldehyde is used in flavoring compounds, perfumes, pharmaceuticals, synthetic resins, rubber accelerators, etc.

In many instances when employing alcoholic feedstocks which are used in the oxidative dehydrogenation of alcohols to form aldehydes, it was necessary to employ alcohols which were anhydrous in nature. However, many processes such as fermentation obtain, as by-products, alcohols which are hydrous in nature and thus form an aqueous alcoholic solution. It has therefore become commercially attractive from an economic standpoint to effect the conversion of aqueous alcoholic solutions to chemical intermediates or other products such as fuels without requiring a stringent preparation process to remove the water before utilizing the alcoholic feedstock.

As will hereinafter be shown in greater detail, it has now been discovered that aqueous alcoholic solutions may be utilized as feedstocks to convert the alcohol to the corresponding aldehyde in an oxidation type reaction involving the use of a certain catalytic composition of matter without appreciably influencing the catalytic properties of said compositions of matter, especially in the retention of catalyst activity, selectivity, stability, etc.

BRIEF DESCRIPTION OF THE INVENTION

This invention relates to a process for the conversion of alcohols to aldehydes. More specifically, the invention is concerned with a process for the catalytic conversion of hydrous alcohols to form the corresponding aldehyde by employing certain catalytic compositions of matter which will enable the conversion process to be effected under relatively mild reaction conditions.

As hereinbefore set forth, it has now been discovered that certain catalytic compositions of matter may be effectively employed in a conversion reaction which involves the treatment of a hydrous alcohol or an aqueous alcoholic solution with an oxygen-containing gas whereby said alcohol is converted to the corresponding aldehyde in a relatively high conversion per pass and selectivity to the desired product. The catalysts which are employed for this reaction will comprise a mixture of at least two oxides composited on a solid support, said catalysts possessing the desirable characteristics which include high activity, high selectivity, high stability and relatively low cost when compared to previously used catalysts which employ the noble metals such as silver, platinum, palladium, etc.

It is therefore an object of this invention to provide a process for the conversion of a hydrous alcohol to an aldehyde.

A further object of this invention is to provide a relatively inexpensive process for conversion of a hydrous alcohol to an aldehyde by employing certain catalytic compositions of matter.

In one aspect, an embodiment of this invention resides in a process for the conversion of an alcohol to the corresponding aldehyde which comprises treating an aqueous alcoholic solution with an oxygen-containing gas at treating conditions in the presence of a catalyst comprising at least two oxides of metals selected from the group consisting of molybdenum, tungsten, cobalt, nickel, manganese, iron and chromium, one of said oxides being molybdenum oxide or tungsten oxide, composited on a high surface area support, and recovering the resultant aldehyde.

A specific embodiment of this invention is found in a process for the conversion of an aqueous ethanol solution which contains from about 1% to about 10% by weight of water to acetaldehyde which comprises treating said aqueous ethanol solution with air in the presence of a catalyst comprising molybdenum oxide, nickel oxide, and manganese oxide composited on gamma-alumina at a temperature in the range of from about 200° to about 400° C., a pressure in the range of from about atmospheric to about 50 atmospheres and a Liquid Hourly Space Velocity in the range of from about 1 to about 10, and recovering the resultant acetaldehyde.

Other objects and embodiments will be found in the following further detailed description of the invention.

DETAILED DESCRIPTION OF THE INVENTION

As hereinbefore set forth, the present invention is concerned with a process for converting an alcohol, and particularly a hydrous alcohol such as that found in an aqueous alcoholic solution, to the corresponding aldehyde utilizing certain catalytic compositions of matter whereby a high rate of conversion of the alcohol to the corresponding high selectivity of a desired product, namely an aldehyde, may be obtained without having to perform a separation process prior to said conversion process whereby the water which is present in the solution is separated from the alcohol. Another advantage which may be obtained by effecting the conversion of the present invention is that the conversion process may be effected while employing operating parameters of temperature and pressure which are less severe than those which have heretofore been employed as well as using a catalyst which is less expensive to manufacture or produce.

The conversion of the alcohol to the corresponding aldehyde will be effected under operating conditions which will include a temperature in the range of from about 200° to about 400° C. and a pressure which may range from atmospheric up to about 50 atmospheres or more while employing Liquid Hourly Space Velocities which may range from about 1 to about 10 or more. In the preferred embodiment of the invention, the operating temperatures may range from about 225° up to about 300° C., while operating the process at atmospheric pressure. Inasmuch as the preferred operating parameters are relatively mild in nature, it is possible to utilize apparatus which, in itself, may be relatively inexpensive, the use of atmospheric pressure obviating the necessity for pressure-resistant articles of equipment such as autoclaves, etc.

The alcohols which are converted to the corresponding aldehydes may comprise those containing from 1 to about 10 carbon atoms in the aliphatic chain, said chain itself being straight or branched in configuration, and preferably those alcohols which contain from 1 to about 4 carbon atoms. Some specific examples of alcohols which may be converted to the corresponding aldehydes will include methanol, ethanol, n-propanol, isopropanol, n-butanol, secbutanol, t-butanol, n-pentanol, sec-pentanol, the corresponding hexanols, heptanols, octanols, nonanols, decanols, etc. These alcohols will be present in a hydrous state such as in an aqueous alcoholic solution which may contain from about 1% to about 10% or more by weight of water, the alcohols themselves being obtained as a result of other chemical reactions such as fermentation, etc. The conversion of these alcohols to the corresponding aldehydes is effected by treating the hydrous alcoholic solution with an oxygen-containing gas which may comprise oxygen, air, or mixtures of oxygen with inert gases such as nitrogen, helium, argon, etc. in the presence of a catalytic composition of matter which comprises at least two metal oxides composited on a solid support at reaction conditions heretofore set forth.

The catalytic composition of matter which may be used to effect the desired conversion of the hydrous alcohol to the aldehyde comprises at least two oxides of metals selected from the group consisting of molybdenum, tungsten, cobalt, nickel, manganese, iron, chromium, at least one of said oxides being molybdenum oxide or tungsten oxide, composited on a high surface area support. The high surface area support, in the preferred embodiment of the invention, comprises an inorganic oxide which possesses a surface area in the range of from about 1 to about 500 m²/g. Some specific inorganic oxide supports which may be employed as the base for the mixture of metal oxides will include various aluminas such as gamma-alumina, eta-alumina, theta-alumina, silica, zeolites, mixtures of inorganic oxides such as alumina-silica, alumina-zirconia, alumina-magnesia, alumina-zirconia-silica, etc.

The aforementioned oxides of the metals set forth in the aforementioned class will be composited on the solid support in a total amount which may range from about 5% to about 25%. Generally speaking, the oxide of molybdenum or tungsten which comprises an essential component of the catalytic composition of matter will be present in an amount in the range of from about 3% to about 20%, the remainder of the total metal oxide comprising either one or more of the aforesaid metal oxides.

Some specific examples of the catalytic components which may be employed to effect the conversion of alcohols to corresponding aldehydes will include molybdenum oxide, nickel oxide and manganese oxide composited on gamma-alumina, tungsten oxide, nickel oxide and manganese oxide composited on gamma-alumina, molybdenum oxide, cobalt oxide and manganese oxide composited on gamma-alumina, molybdenum oxide, chromium oxide and nickel oxide composited on gamma-alumina, tungsten oxide, manganese oxide and ferric oxide composited on gamma-alumina, etc. It is to be understood that the aforementioned catalysts are only representative of the type of composites which may be employed in the conversion process and that the present invention is not necessarily limited thereto.

The process of this invention may be effected in any suitable manner and may comprise either a batch or continuous type operation. For example, when a batch type operation is used, the quantity of the catalyst comprising at least two metal oxides of the type hereinbefore set forth, at least one of the metal oxides being molybdenum oxide or tungsten oxide composited on a solid support, is placed in an appropriate apparatus. This apparatus may comprise a tube reactor, a pressure-resistant vessel such as an autoclave, etc. The alcohol which is to undergo conversion is charged to the reactor along with the oxygen-containing gas. One embodiment of the invention contemplates that the hydrous alcohol and oxygen-containing gas such as air may be charged to the reaction vessel as a mixture such as air saturated with methanol, ethanol, etc. or, if so desired, the hydrous alcohol and oxygen-containing gas may be charged to the reactor through separate means. The reactor may be preheated to the desired operating temperature prior to receiving the alcohol and oxygen-containing gas or, if so desired, the charge stock may be added to the reactor which is subsequently heated to the desired operating temperature. After the hydrous alcohol and oxygen-containing gas have been in contact with the catalyst for a predetermined period of time which may range from about 0.5 up to about 4 hours or more in duration, the reaction product is recovered and subjected to conventional means of separation such as fractional distillation, etc. whereby the desired aldehyde is separated from any side reaction products which may have formed such as acids, ethers, esters, etc., and recovered.

It is also contemplated within the scope of this invention that the conversion process whereby a hydrous alcohol is converted to an aldehyde may be effected in a continuous manner of operation. When such a type of operation is employed, a catalyst of the type hereinbefore described is placed in an appropriate apparatus which is maintained at the proper operating conditions of temperature and pressure. The hydrous alcoholic feedstock is continuously charged to the reactor as is the oxygen-containing gas. As in the description of the batch type operation, the oxygen-containing gas and hydrous alcohol may be charged to the reactor as a mixture in a single stream or, alternatively, the hydrous alcohol and oxygen-containing gas may be admitted to the reactor through separate means. After passage through the reactor for the desired operational time, the reactor effluent is continuously withdrawn and again subjected to the conventional means of separation whereby the desired aldehyde product is separated and recovered, any unreacted alcohol which is recovered from the separation being recycled to the reactor to form a portion of the feedstock.

Inasmuch as the catalyst which is used to effect the reaction is solid in nature, the continuous type of operation may be effected in various ways. One way of effecting the reaction is to employ the catalyst as a fixed bed in the reactor while passing the alcohol and oxygen-containing gas over the catalyst in either an upward or downward flow. Another method of effecting the desired conversion reaction is to employ a moving bed type of operation in which the catalyst moves through the reactor while the alcohol and oxygen-containing gas contact the catalyst in either a concurrent or counter-current flow. Yet another method of effecting a continuous type of operation comprises the slurry type in which the catalyst is carried into the reactor as a slurry in the alcohol feedstock and is continuously removed along with the reaction product.

The conversion of the hydrous alcohols containing from 1 to 10 carbon atoms will result in obtaining useful chemical compounds such as formaldehyde, acetaldehyde, propionaldehyde, butyraldehyde, valeraldehyde, caproaldehyde, heptylaldehyde (oenanthole), caprylaldehyde, pelargonaldehyde, carpaldehyde, etc.

The following examples are given for purposes of illustrating the process of the present invention. However, it is to be understood that these examples are given merely for purposes of illustration and that the present process is not necessarily limited thereto.

EXAMPLE I

A catalytic composition of matter which comprises a mixture of 9% by weight of molybdenum, 2.5% by weight of nickel and 2.5% by weight of manganese which was composited on a gamma-alumina base was placed in a tube reactor in an amount of 0.5 gram, the catalyst having been crushed to a mesh size of from 30 to 35. Following this, a stream of air which was saturated with anhydrous ethanol at a rate of 50 cc/min. was passed over the catalyst at a Liquid Hourly Space Velocity of 0.9 hrs.$^{-1}$ while the reactor was maintained at a temperature of 250° C. and atmospheric pressure. The effluent from the reactor was condensed on a dry ice bed and collected over two hours reaction time. Analysis of the product determined that there had been an 89% conversion of the ethanol with an 83% mole fraction selectivity to acetaldehyde, the reaction by-products consisting of minor amounts of water, acetic acid, ethyl acetate, methyl acetate, methanol, along with traces of methyl-oxy and ethyl-oxy-containing compounds.

EXAMPLE II

To illustrate the ability of the catalyst to effectively convert a feedstock comprising an aqueous alcoholic solution while maintaining a high selectivity rate was illustrated by loading 0.5 gram of the catalyst described in Example I above into a tubular reactor and charging thereto an ethanol vapor feed which was produced by saturating air with an aqueous ethanol solution containing 90% ethanol and 10% water, the saturation of the air being effected at a rate of 50 cc/min. The aqueous alcoholic feed was charged to the reactor at a Liquid Hourly Space Velocity of 0.83 hrs.$^{-1}$ based on the ethyl alcohol, while maintaining the reactor at a temperature of 250° C. and atmospheric pressure. Again, as in Example I, the reactor effluent was condensed on a dry ice bed and analyzed by means of gas chromatography. Analysis of the effluent which was recovered from the reactor over a period of two hours disclosed an 85% conversion of the ethanol with an 85% mole fraction selectivity to acetaldehyde, the remainder of the by-products being substantially similar in nature to those set forth above.

EXAMPLE III

To illustrate the stability of the catalyst to effectively convert an aqueous alcoholic solution to the corresponding aldehyde, the reactions as described in Examples I and II above were carried out for a period of seven hours rather than the two hours time which was employed in these examples. Again, an ethanol vapor feed comprising air saturated with 100% ethanol was utilized as the feed in the first experiment, labeled "A", while the feed employed in the second experiment, which was labeled "B", consisted of air saturated with an aqueous ethanol solution containing 90% ethanol and 10% water. The reactor effluents from both tests were collected on a dry ice bed and analyzed by means of gas chromatography. The results of this seven-hour test were set forth in Table I below.

TABLE I

|  | A | B |
|---|---|---|
| Conversion (%) | 91 | 84 |
| Selectivity to acetaldehyde (%) | 84 | 84 |

It is therefore readily apparent that a feedstock which contains 10% or more by weight of water may be employed in a conversion reaction in which the alcoholic portion of the feedstock is converted to the corresponding alcohol by treatment with an oxygen-containing gas, the ability of the catalyst to effectively convert the alcohol while maintaining an acceptable selectivity to the aldehyde being virtually the same in each instance.

EXAMPLE IV

When other aqueous alcoholic solutions in which methanol, propanol and butanol are present in an amount ranging from about 90% to about 99% by weight of the solution are subjected to a conversion reaction utilizing other conversion catalysts such as tungsten oxide, nickel oxide, and manganese oxide composited on gamma-alumina or a mixture of molybdenum oxide, cobalt oxide and manganese oxide composited on gamma-alumina at a reaction temperature of about 250° C. and a Liquid Hourly Space Velocity of about 1 hr.$^{-1}$, the aforesaid alcohols may be converted to the corresponding aldehydes such as formaldehyde, propionaldehyde and butylaldehyde, respectively.

We claim as our invention:

1. A process for the conversion of ethanol to acetaldehyde in the presence of water which comprises reacting said ethanol, present in an aqueous solution having from about 1% to about 10% by weight water, with an oxygen-containing gas at a temperature in the range of from about 200° to about 400° C., a pressure in the range of from about atmospheric to about 50 atmospheres and a Liquid Hourly Space Velocity in the range of from about 1 to about 10 in the presence of a catalyst consisting essentially of an oxide of molybdenum, an oxide of nickel and an oxide of manganese on a high surface area inorganic oxide support to prepare said acetaldehyde, which is recovered as the reaction product, from said ethanol.

2. The process as set forth in claim 1 in which said oxygen-containing gas is oxygen.

3. The process as set forth in claim 1 in which said oxygen-containing gas is air.

4. The process as set forth in claim 1 in which said high surface area inorganic oxide support is an alumina.

5. the process as set forth in claim 4 in which said alumina is gamma-alumina.

* * * * *